(12) United States Patent
Kindlein et al.

(10) Patent No.: US 7,507,197 B2
(45) Date of Patent: Mar. 24, 2009

(54) URETHRAL PROVE DEVICE FOR EFFECTING RADIATION TREATMENT

(75) Inventors: Johann Kindlein, Oberhausen (DE); Wilco Van Der Lugt, Tiel (NL); Arie Luite Visscher, Driebergen (NL)

(73) Assignee: Nucletron B.V., Veenendaal (NL)

( * ) Notice: Subject to any disclaimer, the term of this patent is extended or adjusted under 35 U.S.C. 154(b) by 362 days.

(21) Appl. No.: 10/615,844

(22) Filed: Jul. 10, 2003

(65) Prior Publication Data
US 2004/0010301 A1 Jan. 15, 2004

(30) Foreign Application Priority Data
Jul. 11, 2002 (EP) .................................. 02077799

(51) Int. Cl.
*A61N 5/00* (2006.01)
(52) U.S. Cl. ........................................................ 600/3
(58) Field of Classification Search ................. 600/1–8, 600/30, 407, 424, 427, 135; 604/19, 27, 604/28, 48, 93.01, 96.01, 158, 161, 163, 604/164.01, 164.08, 506, 514–517; 606/13–14, 606/41
See application file for complete search history.

(56) References Cited

U.S. PATENT DOCUMENTS

| | | | | |
|---|---|---|---|---|
| 5,135,531 A | * | 8/1992 | Shiber ......................... 606/159 |
| 5,139,473 A | * | 8/1992 | Bradshaw et al. .............. 600/3 |
| 5,257,979 A | * | 11/1993 | Jagpal ......................... 604/272 |
| 5,536,240 A | * | 7/1996 | Edwards et al. ................ 604/22 |
| 5,569,220 A | * | 10/1996 | Webster, Jr. .................. 604/527 |
| 6,391,026 B1 | * | 5/2002 | Hung et al. ..................... 606/41 |
| 6,454,696 B1 | * | 9/2002 | Kindlein et al. ................. 600/7 |
| 6,599,237 B1 | * | 7/2003 | Singh ......................... 600/114 |
| 2002/0173689 A1 | * | 11/2002 | Kaplan ......................... 600/7 |
| 2003/0091641 A1 | * | 5/2003 | Tiller et al. ................. 424/486 |

OTHER PUBLICATIONS

Soanes, Catherine, "Compact Oxford English Dictionary of Current English: 3rd Edition", Jun. 23, 2005, Oxford University Press, 11th Edition.*
Merrian-Webster Inc., "Merrian-Webster Online Dictionary", 2005.*

* cited by examiner

*Primary Examiner*—Charles A Marmor, II
*Assistant Examiner*—Christine D Hopkins
(74) *Attorney, Agent, or Firm*—Birch, Stewart, Kolasch & Birch, LLP

(57) ABSTRACT

A device for effecting radiation treatment of benign or malign prostate hyperplasia. The device includes a catheter probe having an elongated body with a circumferential surface which is inserted within the urethra towards the prostate. The elongated body has a longitudinal bore extending towards at least one outlet opening present in the circumferential surface near the proximal end. A catheter tube is inserted with a proximal sharp end through the longitudinal bore of the elongated body, with an outlet opening and through the urethral wall towards a desired location within the prostate. A pre-planned amount of radiation is delivered via the catheter tube at a location within the prostate for effecting the radiation treatment. The urethral insertion probe allows a quick and accurate positioning of the catheter probe and the catheter tube relative to the prostate without discomforting the patient. The catheter probe is movably accommodated within the urethral probe.

22 Claims, 3 Drawing Sheets

URETHRAL PROVE DEVICE FOR EFFECTING RADIATION TREATMENT

BACKGROUND OF THE INVENTION

The invention relates to a device for effecting radiation treatment of benign or malign prostate hyperplasia in a prostate of a human male having a bladder with a base and a penis with an urethra having an urethral wall extending from the base of the bladder through the prostate, said device comprising:

a catheter probe having an elongated body with a circumferential surface, a distal end and a proximal end, which catheter probe is to be inserted with its proximal end within the urethra towards the prostate;

said elongated body of said catheter probe having a longitudinal bore extending from said distal end towards at least one outlet opening present in said circumferential surface near said proximal end;

a catheter tube having a distal end and a proximal sharp end, which catheter tube is to be inserted with its proximal sharp end through said longitudinal bore of said elongated body, said outlet opening and through said urethral wall towards at least one desired location within the prostate to be treated; and means for delivering a certain pre-planned amount of radiation energy via said catheter tube near or at said at least one location within said prostate for effecting said radiation treatment.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

DISCUSSION OF THE BACKGROUND

Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention.

An example of a surgical approach for the treatment of benign prostatic hypertrophy is known from U.S. Pat. No. 5,536,240, wherein an urethral probe device according to the above introduction is disclosed.

A drawback of this known urethral probe device is, that for each subsequent radiation session the device has to be repositioned within the urethra in order to position the electromagnetic electrode towards a new location within the prostate. The repositioning of the probe device within the urethra will cause damage to the urethra wall tissue, thus discomforting the patient. Moreover the location of the prostate within the lower male anatomy will be changed during repositioning the urethral probe device, requiring the necessity of relocating the exact positioning of the prostate, e.g. with the use of ultrasound imaging means.

In U.S. Pat. No. 5,536,240 an catheter probe is inserted into the urethra and moved towards the prostate of the patient to be treated. The probe end which is nearest the prostate when inserted into the urethra is provided with one or more openings, through which an hollow flexible needle can be guided, which needle is inserted through the hollow catheter probe and subsequently inserted at a desired location within the prostate. The needle herewith perforates the urethral wall. In one embodiment according to U.S. Pat. No. 5,536,240 the needle is constructed as an radio frequency electrode for emitting electromagnetic energy towards the prostate for treatment of the cancerous tissue within the prostate.

In the event that the prostate is subjected to multiple subsequent treatment sessions, the needle is retracted from its initial position in the prostate into the catheter probe, afterward the catheter probe is displaced within the urethra towards the next treatment position relative to the prostate. Subsequently the radio frequency electrode is advanced through the urethral wall towards its new radiation position within the prostate.

A major drawback of the known urethral probe device according to U.S. Pat. No. 5,536,240 is the need for reorientating the probe device within the urethra towards a new treatment position relative to the prostate. The repositioning of the catheter probe within the urethra causes discomfort to the patient due to the advancing and retracting movements within the urethra. Furthermore the positioning and repositioning of each needle for emitting a certain amount of electromagnetic radiation towards the cancerous tissue of the prostate is inaccurate, resulting in a less accurate treatment of the prostate.

An example of a device for effecting radiation therapy in an animal body by implanting radioactive seeds through a number of needles inserted in the animal body is for example disclosed in European patent application no. EP-A1-1 070 519. See also FIG. 1 of the drawings. Prior to implanting the radioactive seeds, in that device one or more hollow needles 9, 110 are inserted via a template 115 into the animal body 111, wherein the exact location of the (tip of the) needle is monitored using images obtained with an intracavitary ultrasound probe 7, which probe is inserted into the patient's rectum. The needle insertion means 118 as well as the means 113, which move the probe 7 are controlled using information obtained from said images.

SUMMARY OF THE INVENTION

It is an object of the invention to provide an urethral insertion probe which allows a quick and more accurate positioning of the catheter probe and the catheter tube relative to the prostate without discomforting the patient.

It is a further object of the invention to provide an urethral probe device which is capable of automatically position and insert a needle through the catheter probe into the prostate and further for quickly and precise positioning one or more energy emitting sources through said needle at the desired location within the prostate in case of malign hyperplasia treatment.

It is a further object of the invention to provide an urethral probe device of an less complicated and cheaper construction.

According to the invention the device for effecting treatment of benign or malign prostate hyperplasia in a prostate of a human male is characterised in that said catheter probe is movable accommodated within an urethral probe to be inserted within said urethra.

An urethral probe is inserted within the urethra prior to the insertion of the catheter probe, which urethral probe remains during the treatments in a static, unmovable position within the urethra. The catheter probe is subsequently moveable accommodated within said urethral probe and makes it possible to displace the catheter probe within the urethral probe towards each position relative to the prostate. Due to the fact that the catheter probe is moveable accommodated within an urethral probe which is positioned in a fixed manner within the urethra during the treatment sessions, the patient is no longer discomforted.

A more quick and precise orientation of the catheter probe and thus the catheter tube for insertion into the prostate relative to the prostate according to the invention that said catheter probe is movable in longitudinal and/or rotational direction within said urethral probe.

According to a specific embodiment of the urethral insertion probe device according to the invention said urethral probe consists of an elongated probe body having a distal end and a proximal end to be inserted within said urethra, said elongated probe body being provided with a longitudinal urethral probe bore for accommodating said catheter probe.

For a smooth guidance and positioning of the catheter probe within the urethral probe, are according to the invention the inner dimensions of said longitudinal urethral probe bore equal or slightly larger than the outer dimensions of said catheter probe.

Preferably the catheter probe drive means are present for moving said catheter probe in longitudinal and/or rotational direction within said urethral probe, whereas for a quick and accurate insertion of the catheter tube into the prostate according to the invention the catheter tube drive means are present for moving said catheter tube in longitudinal direction within said catheter probe.

In order to facilitate the proper positioning of the catheter tube inside the prostate according to the invention said catheter tube is a flexible tube having a sharp proximal end.

In a specific embodiment, wherein said energy emitting source can be positioned inside the prostate in a quick, accurate and safe manner, said means for delivering said radiation energy comprise at least one wire having a distal end and a proximal end; and at least one energy emitting source to be inserted by means of said proximal end of said wire through said catheter tube towards said location within the prostate to be treated. In a further embodiment of the urethral probe device according to the invention said means for delivering said radiation energy further comprise means for inserting said at least one energy emitting source within said catheter tube. This allows a proper, safe and accurate handling of the energy emitting source towards the patient, without exposing for example the medical personal to the radiation emitted by said energy emitting source.

A fully automated, more or less computer controlled operation of the urethral probe device according to the invention can be obtained whereas according to the invention said means for delivering said radiation energy furthermore comprise wire drive means for moving said wire together with said at least one energy emitting source through said catheter tube towards said location within the prostate to be treated.

In a specific embodiment of the device according to the invention said elongated body of said urethral probe is made of a flexible material. This allows a smooth and guided insertion of the urethral probe into the urethra without discomforting the patient.

In an other embodiment said urethral probe is made of a partly ridged material.

In an other specific embodiment of the urethral probe device according to the invention said elongated body of said urethral probe is build as a grating of a plurality of filaments, wherein said filaments are made of a rubber material or bioabsorbable material or wherein said filaments are made of a metal material. In the latter embodiment said grating of said plurality of metal filaments is provided with a tissue friendly coating, e.g. a rubber material coating, wherein preferably said rubber material coating is made of polyurethane.

The use of the urethral probe made of the materials mentioned above allows an arbitrary positioning of the catheter probe within the urethral probe and the insertion of a catheter tube at an arbitrary position within the prostate to be treated. This allows a more flexible use of the urethral probe device according to the invention in relation to the known devices such as the urethral probe device disclosed in U.S. Pat. No. 5,536,240. Moreover the materials used for the urethral probe are tissue friendly resulting in a subsequent less discomforting radiation treatment sessions for the patient.

A fully automatic computer controlled treatment of the prostate of a human male can be performed when according to the invention the insertion and positioning of said catheter tube, and/or said proximal needle, and/or said wire together with said at least one energy emitting source through said catheter probe towards said at least one desired location within the prostate to be treated is monitored and controlled using imaging information delivered by imaging means positioned within the rectum of the human male. This avoids the manual positioning of the catheter probe within the urethra by the medical personal and thus avoids a less accurate positioning of the catheter tubes and the energy emitting sources within the prostate.

The accuracy, and precise positioning of the catheter probe relative to the prostate is further improved, when according to the invention the catheter probe drive means for positioning said catheter probe within said urethral probe are controlled by means said imaging means and at least one computer planning treatment system.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
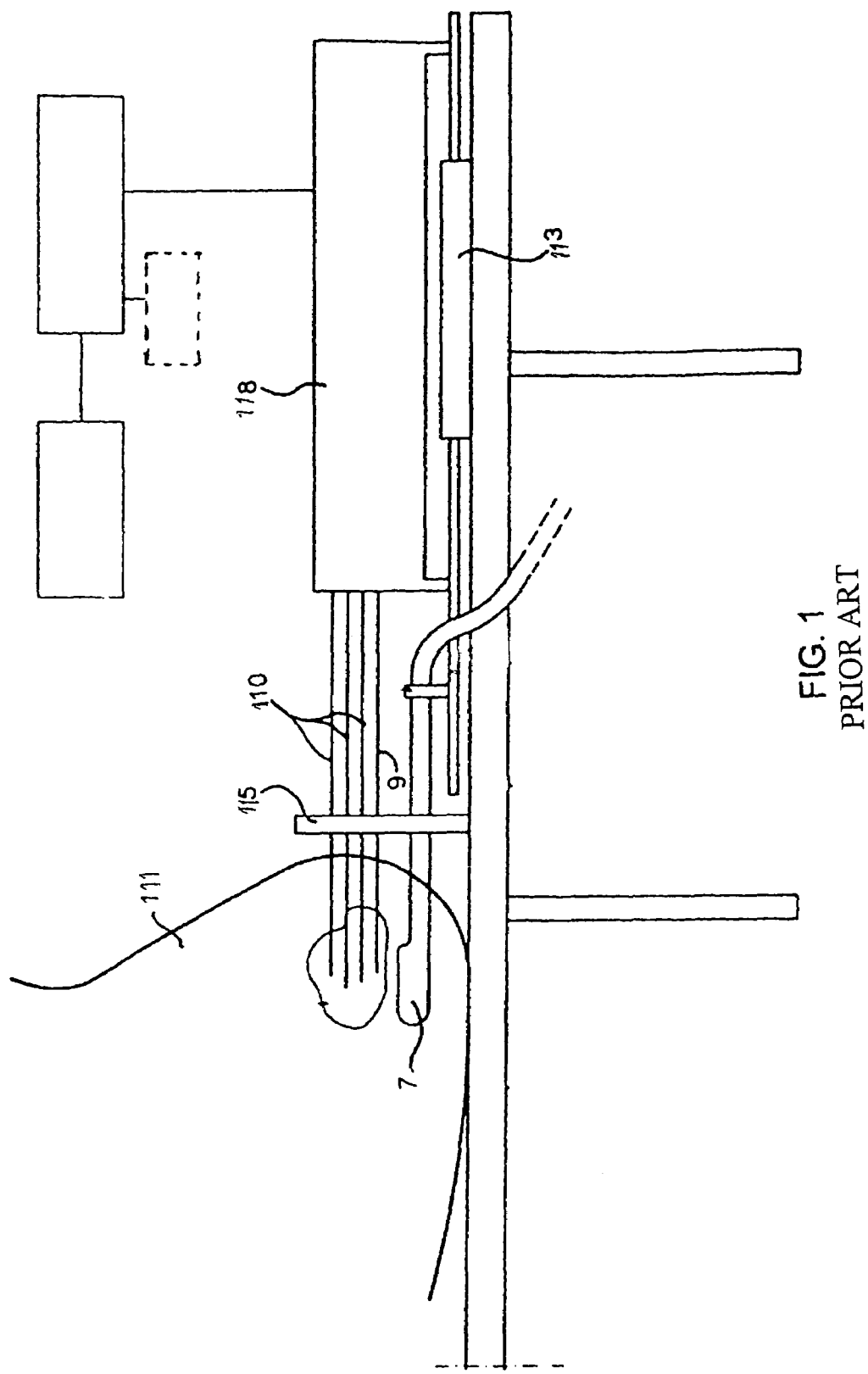
FIG. 1 an embodiment of a device for effecting radiation therapy in an animal body by implanting radioactive seeds through a number of needles inserted in the animal body according EP-A1-1070519.
Figure 2:
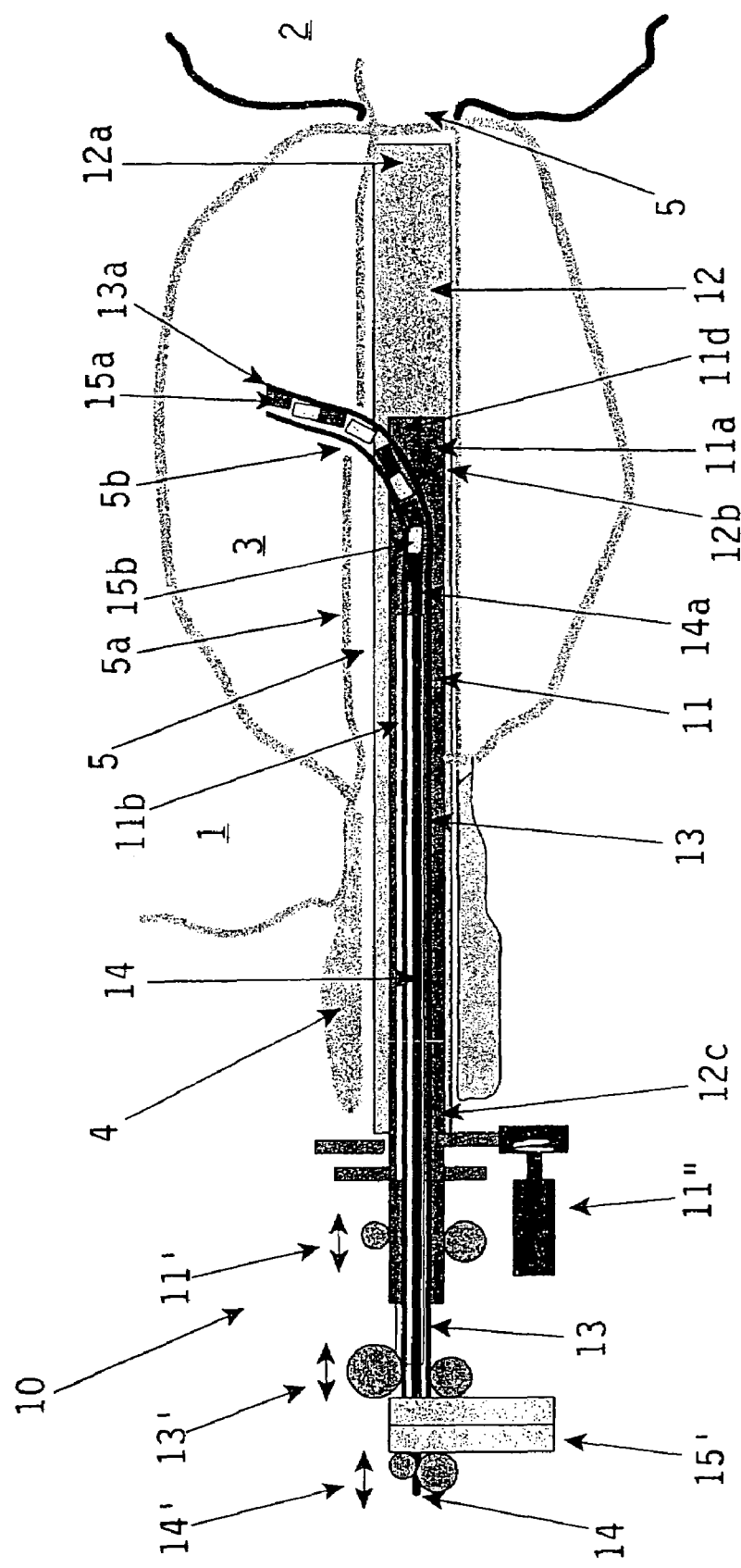
FIG. 2 an embodiment of an urethral probe device according to the invention.

Referring now to the drawings, wherein like reference numerals designate identical or corresponding parts throughout the several views and more particularly to FIG. 2 which shows a schematic cross-sectional drawing of the lower male anatomy during use of the urethral probe device according to the invention. The urethra 5 extends from the urinary bladder 2 through the prostate 3 and through the penis 4. Traditional treatments apart from the removal of the prostate have included either a removal of tissue from the urethra 5 to enlarge its lumen by resection or laser tissue destruction or by expansion and heating of the tissue surrounding the urethra 5 to the temperature, which causes cell death. The latter method is intended to reduce the swelling or enlargement of the prostate 3 and to restore the urinary passage to at least the portion of its former diameter.

For the treatment of the prostate the probe device 10 according to the invention comprises an urethral probe 12 which is inserted from the penis 4 through the urethra 5 into the prostate 3. The urethra probe 12 is inserted into the urethra 5 with its proximal end portion 12a to be positioned near the base of the bladder 2, whilst the distal end portion 12c remains exposed outside the penis 4 of the patient. The urethral probe having its elongated body will stay fix during the treatment of benign or malign prostate hyperplasia.

The urethral probe 12 is provided with a longitudinal bore 12b which extends from the distal end portion 12c through the elongated body of the urethral probe 12 and ends at a certain distance from the proximal end portion 12a near the prostate 3. Through said longitudinal bore 12b a catheter probe 11 is to be inserted from the distal end portion 12c toward the prostate 3, until the catheter probe 11 completely occupied and fills the longitudinal bore 12b in the urethral probe 12. Preferably the inner dimensions of said longitudinal urethral probe bore 12b are equal or slightly larger than the outer dimensions of said catheter probe 11. More preferably are the dimensions of both the urethral probe bore 12b and the catheter probe 11 of a circular shape, which function will explained further in the description.

Figure 3:
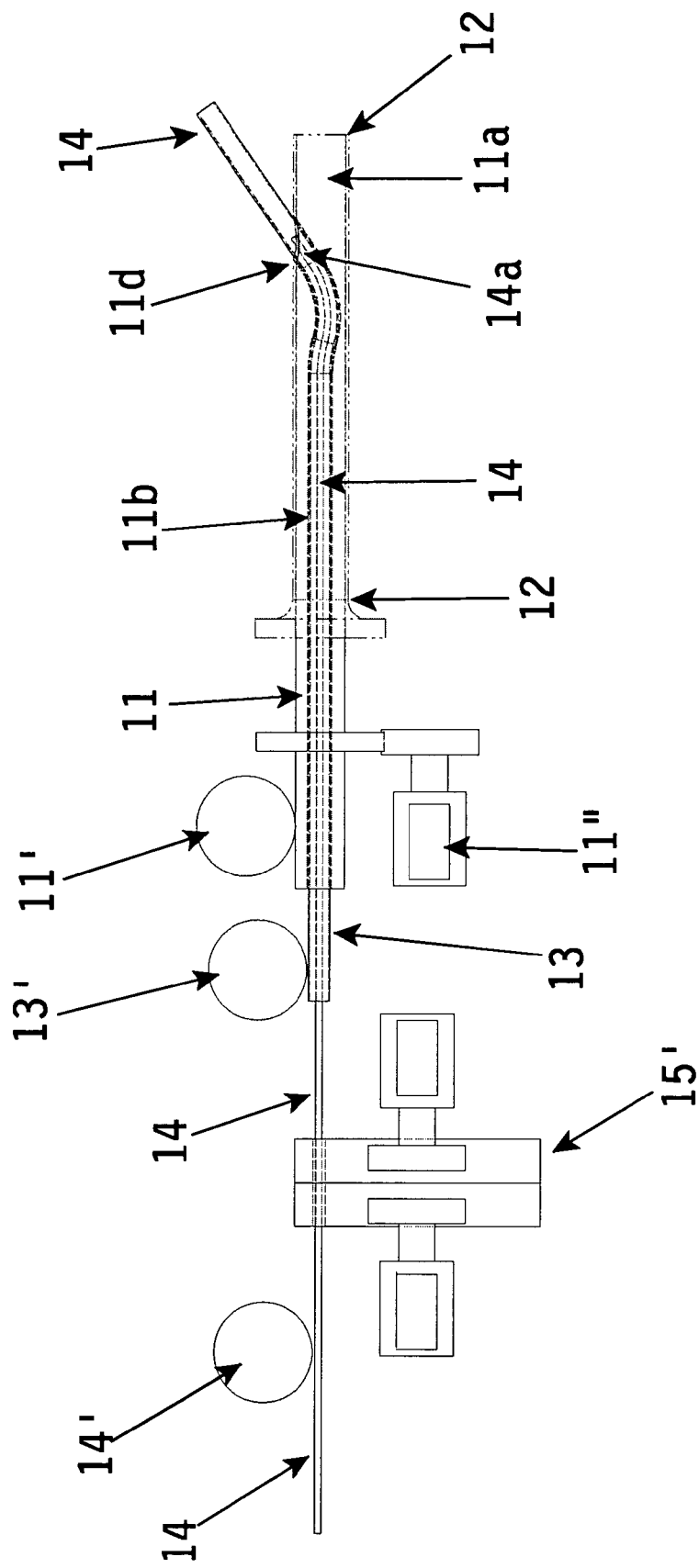
FIG. 3 an enlarged view of the urethral probe device of FIG. 2.

The catheter probe 11 comprises a longitudinal bore extending from said catheter probe distal end 12c toward at least one outlet opening 11d present in the circumferential surface of the catheter probe 11. Said outlet opening 11d is located near the proximal end 11a of the catheter probe 11. As the outlet opening 11d is present on the circumferential surface of the catheter probe 11 the longitudinal catheter probe bore 11b has the shape of a curved passageway near the proximal end 11a of the catheter probe 11. See also FIG. 3.

Whereas the urethral probe 12 will stay fix within the urethra 5 during the treatment, said catheter probe 11 is moveable accommodated within the longitudinal probe bore 12b of the urethral probe 12. Due to the circular shape of both the catheter probe 11 and the longitudinal probe bore 12b of the urethra probe 12, whereas the outer dimensions of the catheter probe 11 nearly matches the inner dimensions of the longitudinal probe bore 12b of the urethral probe 12, the catheter probe 11 is capable of moving in both a longitudinal direction as well as in a rotational direction.

According to the invention the urethral probe device 10 is provided with suitable drive means for displacing the catheter probe 11 in a longitudinal direction and/or rotational direction within the longitudinal urethral probe bore 12b. Therefore drive means 11' are present for positioning the catheter probe 11 in a longitudinal direction within the urethral probe 12, whilst drive means 11" are used for rotating the catheter probe 11 within the longitudinal urethral probe bore 12b. Both catheter drive means 11'-11" are used for positioning the outlet opening 11d of the catheter probe bore 11b relative to the prostate 3.

Furthermore the urethral probe device 10 comprises drive means 13' for advancing or retracting in a longitudinal direction a hollow catheter tube 13 through the catheter probe bore 11b and towards said outlet opening 11d. The hollow catheter tube 13 comprises a proximal end 13a which proximal open end 13a is shaped and sharpened as a sharp end (tip). In fact the catheter tube 13 can be a flexible hollow needle, which catheter tube 13, when advanced through said outlet opening 11d of the catheter probe bore 11b, will perforate with its sharp end 13a the urethral wall 5a (in FIG. 2 depicted with reference numeral 5b) until a certain desired location within the prostate 3.

Subsequently through said catheter tube 13 now inserted and positioned within the prostate 3 energy emitting sources, for example one or more radioactive seeds 15a inserted through the catheter tube 13 in the form of a train of subsequent energy emitting seeds 15a and non-energy emitting spacers 15b through the catheter tube 13 towards the pre-plant location within the prostate 3.

The so called train of energy emitting seeds 15a (for example radioactive seeds) and non-radioactive spacers 15b are left behind within the prostate 3 at the desired location, where prostate tissue will be exposed to the radiation energy emitted by said radioactive sources.

The energy emitting sources 15a are inserted towards the desired location within the prostate 3 by means of an wire 14 which is advanced using wire drive means 14' through said catheter tube 13, whereas the proximal end 14a of the wire 14 will push the train of radioactive seeds 15a and non-radioactive spacers 15b through the catheter tube 13 towards the desired radiation treatment position within the prostate 3.

When the train of energy emitting sources 15a and non-radioactive spacers 15b are positioned within the prostate 3, the catheter tube drive means 13' retract the catheter tube 13 and its open sharp end 13a from the prostate 3 back into the catheter probe bore 11b leaving the radioactive sources 15a within the prostate. By emitting electromagnetic radiation due to the natural radioactive decay of the radioactive sources 15a the cancerous tissue of the prostate 3 is exposed and destroyed.

In the above description the treatment of malign hyperplasia has been described by inserting a train of one or more radioactive sources 15a and one or more non-radioactive spacers 15b from the radiation shielded cartridge 15' through a catheter tube 13 having an open end 13a by pushing the train towards the desired position within the prostate 3 using a wire 14, and subsequently retracting the wire 14 and the catheter tube 13 leaving the train of radioactive sources 15a and non-radioactive spacers 15b behind within the prostate.

Treatment of malign hyperplasia can also be performed by using only one energy emitting source 15a, which is connected in a fixed manner to the proximal end 14a of the wire 14. More particularly the energy emitting source 14a can be an high dose rate (HDR) or a pulse dose rate (PDR) energy emitting source. For HDR/PDR-treatment the catheter tube 13 has a closed sharp end 13a, which catheter tube 13 is inserted within the catheter probe bore 11b towards the desired location within the prostate 3. The catheter tube will remain with its sharp end 13a in that position during the treatment. The HDR/PDR-source connected to the proximal end 14a of the wire 14 is inserted/pushed through the hollow catheter tube 13 into the prostate 3 until it reaches the closed end 13a of the catheter tube.

The HDR/PDR-source is maintained in that position for a specified duration after which exposure time the HDR/PDR-source has to be retracted from its location with in prostate 3 through the catheter probe bore 11b back to the radiation shielding 15' using the wire drive means 14'. By subsequently retracting the catheter tube 13 using the catheter tube drive means 13' from the prostate 3 back into the catheter probe bore 11b it is possible to displace the catheter probe 11 in a longitudinal and/or rotational direction within the urethral probe bore 12b using the catheter probe drive means 11'

(longitudinal direction) and/or the catheter probe drive means 11" (rotational displacement). Repositioning the catheter probe 11 in a longitudinal and/or rotational direction within the urethral probe bore 12b will result in a repositioning of the outlet opening 11d of the catheter probe bore 11b relative to the prostate 3.

By subsequently advancing the catheter tube 13 using the catheter tube drive means 13' through the catheter probe bore 11b and the outlet opening 11d through the urethral wall 5a towards a new location within the prostate 3, it is possible to perform multiple, subsequent radiation treatment sessions with the patient as a new train of radioactive seeds 15a and non-radioactive spacers 15b can be transferred from the radiation shielded cartridge 15' into the catheter tube 13b, which train is subsequently displaced to the catheter tube 13 towards the new location within the prostate 3 using the wire 14 and the wire drive means 14'.

In a similar way the HDR/PDR-source previously retracted from its first location within the prostate 3 can be inserted through the catheter tube 13 towards the new location within the prostate 3 for a subsequent radiation treatment session.

In a similar manner benign hyperplasia can be treated using a catheter tube 13 with an open sharp end 13a, which is positioned at a desired location within the prostate 3. In this case the wire could be a flexible tube (nitinol for example) with an inside isolated electrical wire in contact with a RF (radio-frequency) generator. Subsequently an antenna of a variable length emitting radiowaves for heating the tissue to be treated, which antenna is connected in a fixed manner to the proximal end 14a of the wire 14, is inserted through the catheter tube 13 into the prostate. The variable length is obtained by automated modification of the length of the outside part of the antenna in the catheter tube. The catheter tube 13 is then retracted keeping the wire 14 and the antenna in place within the prostate. Subsequently the antenna is activated for treating the benign hyperplasia by emitting radiowaves, which waves induce heat.

Due to the fact that the urethral probe 12 will stay fixed within the urethra of the patient during the radiation treatment of the prostate and the catheter probe 11 is moveable accommodated within the urethral probe bore 12b for repositioning the outlet opening 11d and the catheter tube 13 in each desired location relative to the prostate 3, multiple subsequent treatments can be performed according to the dimensions and shape of the hyperplasia with the same patient without discomforting the patient.

Moreover a more precise and accurate positioning of the energy emitting source through the catheter tube towards each desired location within the prostate can be obtained, as the position of the catheter probe 11 and the catheter tube 13 within the urethra 5 is precisely controlled, using ultrasound information obtained from signals received from a conventional ultrasound imaging probe (not shown) which is inserted into the rectum adjacent to the prostate 3 through the 1-0 opening of the patient. Using ultrasound imaging an easy and accurate and desired positioning of the catheter tube 13 and its sharp end 13a into a precise location within the prostate 3 is herewith obtained.

In order to facilitate the insertion of the catheter tube 13 with its sharp end 13a through the outlet opening 11d through the urethral wall 5a into a desired location within the prostate 3 the urethral probe 12 is preferably made of a flexible material which can be easily perforated by the sharp end 13a of the catheter tube 13. Moreover a flexible urethral probe 12 will provide less discomforted to the patient. More in particularly the urethral probe 12 is made of a tissue friendly material, for example a rubber, a bioabsorbable material or polyurethan, whereas in a specific embodiment the urethral probe 12 is a polyurethan covered stent, which is commercially available.

The stent can be made of for example a grating of a plurality of filaments, which filaments are made of a rubber material of are made of a metal material. In the latter embodiment said grating of said plurality of metal filaments is provided with a tissue friendly coating, for example a rubber material coating and more particularly of a polyurethan coating.

The use of a stent is most advantageously, as the stent allows the catheter tube to be positioned into an arbitrary location within the prostate 3.

Preferably the operation of the urethral probe device is fully computer controlled, whereas the several drive means for the catheter probe 11, the catheter tube 13 and the wire 14 are driven using ultrasound image information obtained from an ultrasound imaging probe inserted into the rectum of the patient in order to position the catheter tube 13 at each desired location within the prostate 3 following a specific radiation treatment plan.

Thus it is possible to insert large numbers of radioactive seeds 15a from the radiation shielded cartridge 15' through the catheter tube 13 using the wire 14 towards multiple locations within the prostate 3, whereas the spatial orientations of the several radiation treatment positions within the prostate 3 are pre-determined by a radiation treatment planning system.

It will be clear from the above description that the urethral probe device according to the invention does not require the manual insertion of the subsequent catheter tubes 13 within the prostate 3 and that each catheter tube can be positioned within the prostate at an arbitrary location within the prostate 3 due to the possibility of positioning the catheter probe 11 in an arbitrary rotational direction and/or an arbitrary longitudinal direction within the urethral probe bore 12b and that it is possible to perform multiple radiation treatment sessions in a sequential order without discomforting the patient.

Whereas the rotational and longitudinal positioning of the catheter probe within the urethral probe bore 12b as well as the insertion of the catheter tube through the catheter probe bore 11b toward each desired location within the prostate 3 and the subsequent insertion of an energy emitting source (radioactive seeds 15a or HDR/PDR-source or radiowaves emitting antenna) through the catheter tube towards said location within the prostate 3 is fully computer controlled using ultrasound imaging information a fast, accurate and versatile new device for performing treatment of benign or malign hyperplasia is provided.

Furthermore the treatment of benign or malign prostate hyperplasia can be performed under only a local anaesthesia which will be also less discomforting for the patient.

The invention claimed is:

1. Device for effecting radiation treatment of benign or malign prostate hyperplasia in a prostate of a human male having a bladder with a base and a penis with an urethra having an urethral wall extending from the base of the bladder through the prostate, said device comprising:
    a urethral probe adapted to be inserted within said urethra;
    a catheter probe having an elongated body with a circumferential surface, a distal end and a proximal end, said catheter probe adapted to be inserted in said urethral probe with its proximal end within the urethra towards the prostate;
    said elongated body of said catheter probe having a longitudinal bore extending from said distal end towards at least one outlet opening present in said circumferential surface near said proximal end;

a catheter tube having a distal end and a proximal sharp end, said catheter tube adapted to be inserted with its proximal sharp end through said longitudinal bore of said elongated body, through said at least one outlet opening and adapted to be inserted through said urethral wall towards at least one desired location within the prostate to be treated;

said urethral probe being made of a material to be perforated by said proximal sharp end of said catheter tube at arbitrary positions relative to the prostate; and means for delivering a certain pre-planned amount of radiation energy via said catheter tube near or at said at least one desired location within said prostate for effecting said radiation treatment, said catheter probe being movably accommodated within said urethral probe.

2. Device according to claim 1, characterized in that said catheter probe is movable in at least one of longitudinal and rotational direction within said urethral probe.

3. Device according to claim 1, characterized in that said urethral probe consists of an elongated probe body having a distal end and a proximal end adapted to be inserted within said urethra, said elongated probe body being provided with a longitudinal urethral probe bore for accommodating said catheter probe.

4. Device according to claim 3, characterized in that the inner dimensions of said longitudinal urethral probe bore are slightly larger than the outer dimensions of said catheter probe.

5. Device according to claim 3, characterized in that said elongated body of said urethral probe is made of a flexible material.

6. Device according to claim 3, characterized in that said urethral probe is made of a partly rigid material.

7. Device according to claim 3, characterized in that said elongated body of said urethral probe is built as a grating of plurality of filaments.

8. Device according to claim 7, characterized in tat said filaments are made of a rubber material or bioabsorbable material.

9. Device according to claim 7, characterized in that said filaments are made of a metal material.

10. Device according to claim 9, characterized in that said grating of said plurality of metal filaments is provided with a rubber material coating.

11. Device according to claim 10, characterized in that said rubber material coating is made of polyurethane.

12. Device according to claim 1, characterized in that catheter probe drive means are present for moving said catheter probe in at least one of longitudinal and rotational direction within said urethral probe.

13. Device according to claim 1, characterized in that catheter tube drive means are present for moving said catheter tube in a longitudinal direction within said catheter probe.

14. Device according to claim 1, characterized in tat said catheter tube is a flexible tube having a proximal sharp end.

15. Device according to claim 14, characterized in that said means for delivering said radiation energy comprise at least one wire having a distal end and a proximal end; and at least one energy emitting source to be inserted by means of said proximal end of said wire through said catheter tube towards said location within the prostate to be treated.

16. Device according to claim 15, characterized in that said means for delivering said radiation energy further comprise means for inserting said at least one energy emitting source within said catheter tube.

17. Device according to claim 16, characterized in that said means for delivering said radiation energy furthermore comprise wire drive means for moving said wire together with said at least one energy emitting source through said catheter tube towards said location within the prostate to be treated.

18. Device according to claim 15, characterized in that the insertion and positioning of said catheter tube, a proximal needle, and said wire together with said at least one energy emitting source through said catheter probe towards said at least one desired location within the prostate to be treated is monitored and controlled by a computer program according to a planning information delivered by a treatment planning program using imaging information delivered by imaging means adapted to be positioned within the rectum of the human male.

19. Device according to claim 18, characterized in that a catheter probe drive means for positioning said catheter probe within said urethral probe is controlled by said imaging means and at least one computer planning treatment system.

20. Device according to claim 15, characterized in that said at least one energy emitting source is a radioactive source.

21. Device according to claim 15, characterized in that said at least one energy emitting source is a high dose rate or pulse dose rate source.

22. Device according to claim 15, characterized in that said at least one energy emitting source is an antenna of a variable length emitting radiowaves.

* * * * *